US00PP33932P2

(12) United States Plant Patent
Kievit et al.

(10) Patent No.: US PP33,932 P2
(45) Date of Patent: Feb. 1, 2022

(54) ***LYSIMACHIA* PLANT NAMED 'FIREFLY'**

(50) Latin Name: *Lysimachia congestiflora*
Varietal Denomination: Firefly

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/460,263

(22) Filed: Aug. 29, 2021

(51) Int. Cl.
*A01H 5/02* (2018.01)
*A01H 6/00* (2018.01)

(52) U.S. Cl.
USPC ..... Plt./453

(58) Field of Classification Search
USPC ..... Plt./453
See application file for complete search history.

*Primary Examiner* — Annette H Para
(74) *Attorney, Agent, or Firm* — Audrey Charles

(57) ABSTRACT

A new and distinct cultivar of *Lysimachia* plant named 'Firefly', characterized by its dark yellow-colored flowers, dark green with dark burgundy colored foliage, and moderately vigorous, spreading growth habit, is disclosed.

1 Drawing Sheet

Latin name of genus and species of plant claimed: *Lysimachia congestiflora.*
Variety denomination: 'Firefly'.

BACKGROUND OF THE INVENTION

The present invention relates to a new and distinct cultivar of *Lysimachia* plant botanically known as *Lysimachia congestiflora* and hereinafter referred to by the cultivar name 'Firefly'.

The new cultivar originated in a controlled breeding program in Hem, the Netherlands during the summer 2015. The objective of the breeding program was the development of *Lysimachia* cultivars for use as an accent plant in a container or a flowering groundcover in shade to partial shade landscapes.

The new *Lysimachia* cultivar is the result of self-pollination. The parent of the new cultivar is the proprietary *Lysimachia congestiflora* breeding selection coded A150, not patented, characterized by its medium yellow-colored flowers, dark green-colored foliage, and vigorous, spreading growth habit. The new cultivar was selected as a single flowering plant within the progeny of the above stated self-pollination during July 2016 in a controlled environment in Hem, the Netherlands.

Asexual reproduction of the new cultivar by terminal stem cuttings since July 2016 in Hem, the Netherlands and West Chicago, Ill. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Firefly' as a new and distinct cultivar of *Lysimachia* plant:

1. Dark yellow-colored flowers;
2. Dark green with dark burgundy colored foliage; and
3. Moderately vigorous, spreading growth habit.

Plants of the new cultivar differ from plants of the parent primarily in having green and burgundy colored foliage, and reduced growth vigor.

Of the many commercially available *Lysimachia* cultivars, the most similar in comparison to the new cultivar is 'Persian Chocolate', not patented. However, in side-by-side comparison, plants of the new cultivar differ from plants of 'Persian Chocolate' in at least the following characteristics:

1. Plants of the new cultivar have shorter leaves than plants of 'Persian Chocolate';
2. Plants of the new cultivar have a leaf color that has less purple coloration under shade conditions than plants of 'Persian Chocolate'; and
3. Plants of the new cultivar are less spreading than plants of 'Persian Chocolate'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Firefly'. The plants were approximately five months old. The plants were grown three plants per pot in three-quart containers for approximately 10 weeks in an outdoor shade nursery in West Chicago, Ill. Plants were given two pinches prior to transplant and one pinch one week after transplant.

DETAILED BOTANICAL DESCRIPTION

Figure 1:
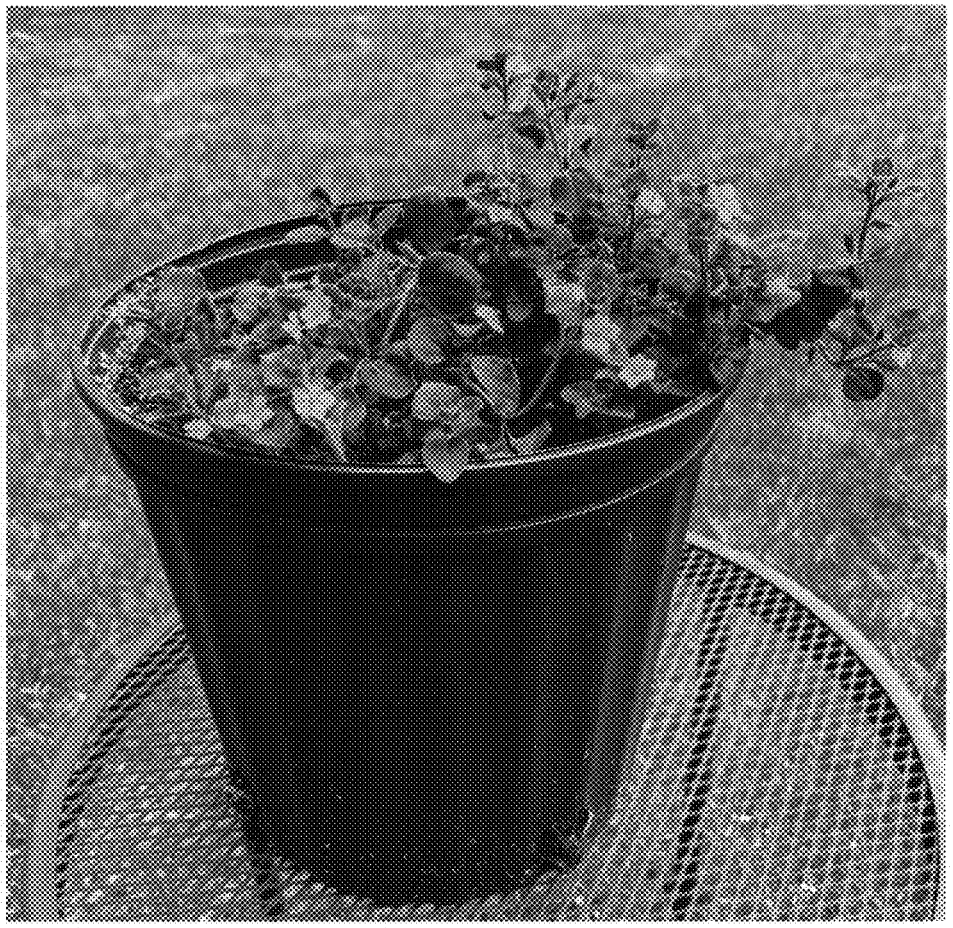
FIG. 1 illustrates a side view of the overall growth and flowering habit of 'Firefly'.
Figure 2:
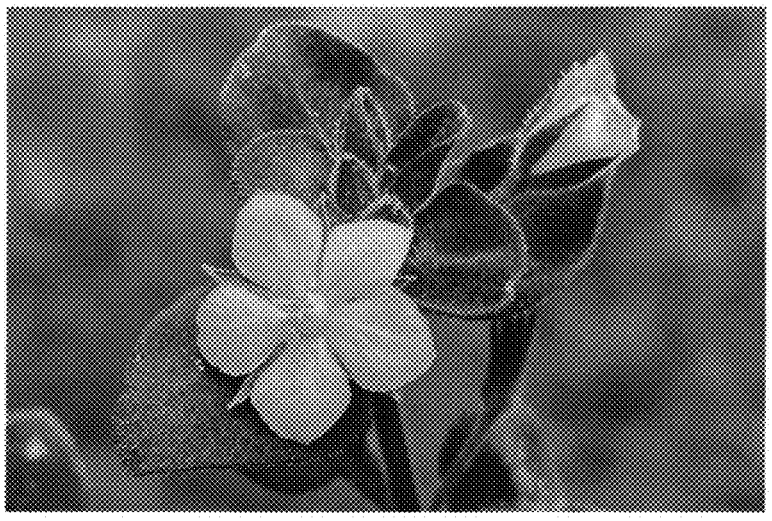
FIG. 2 illustrates a close-up view of an individual flower of 'Firefly'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2021 under natural light conditions in Naperville, Ill.

The following descriptions and measurements describe approximately five- month-old plants produced from cuttings from stock plants and grown under conditions comparable to those used in commercial practice. The plants were grown three plants per pot in three-quart containers for approximately 10 weeks in an outdoor shade nursery in West Chicago, Ill. Plants were given two pinches prior to transplant and one pinch one week after transplant. Prior to transplant plants were grown in liners in a polycovered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Lysimachia congestiflora* 'Firefly'.

Parentage:

*Female and male parent*.—Proprietary *Lysimachia congestiflora* breeding selection coded A150, not patented Propagation:

*Type cutting*.—Terminal stem.

*Time to initiate roots*.—Approximately 7 days.

*Time to produce a rooted cutting*.—Approximately 42 to 49 days.

*Root description*.—Fibrous, fine.

*Rooting habit*.—Freely branching.

Plant description:

*Commercial crop time*.—Approximately 6 to 8 weeks from a rooted cutting to finish in a 10 cm pot.

*Growth habit and general appearance*.—Perennial, flowering groundcover, moderately vigorous, spreading.

*Hardiness*.—USDA Zone 5b (−15° F. to −10° F./−26.1° C. to −23.3° C.).

*Size*.—Height: Approximately 10.0 cm. Width: Approximately 26.0 cm.

*Branching habit*.—Freely basal branching, pinching enhances basal branching. Quantity of main branches per plant: Approximately 11.

*Branch*.—Strength: Strong. Length: Approximately 16.0 cm. Diameter: Approximately 2.0 mm. Length of central internode: Approximately 2.8 cm. Texture: Densely pubescent with a mixture of glandular and nonglandular hairs. Gland color: Colorless, transparent. Color of young and mature stems: 146C with a heavy overlay of 187A.

Foliage description:

*General description*.—Quantity of leaves per branch: Approximately 10 Fragrance: None detected. Form: Simple. Arrangement: Opposite.

*Leaves*.—Aspect: Perpendicular to oblique angle to stem. Shape: Deltoid to orbicular. Margin: Entire. Apex: Broadly acute to obtuse. Base: Truncate to rounded. Venation pattern: Pinnate. Length of mature leaf: Approximately 2.3 cm. Width of mature leaf: Approximately 2.3 cm. Texture of upper surface: Moderately pubescent, bullate. Texture of lower surface: Densely pubescent with a mixture of glandular and nonglandular hairs. Gland color: Colorless, transparent. Color of upper surface of young foliage: NN137A with a heavy overlay of 187A, venation indistinguishable except for basal portion of midvein of 146C. Color of lower surface of young and mature foliage: Closest to 147C mottled with 187A, venation indistinguishable. Color of upper surface of mature foliage: NN137A tinted with 187A, venation indistinguishable except for basal portion of midvein of 146C.

*Petiole*.—Length: Approximately 4.0 mm. Diameter: Approximately 2.0 mm. Texture: Moderately pubescent. Color: Closest to 147C mottled with 187A.

Flowering description:

*Flowering habit*.—'Firefly' is freely flowering under outdoor growing conditions with substantially continuous blooming from spring through late summer.

*Lastingness of individual flower on the plant*.—Approximately 7 to 10 days.

Flower description:

*General description*.—Type: Single, upward to outward facing, nyctinastic. Quantity: Approximately 23. Arrangement: Solitary in leaf axil.

*Bud*.—Rate of opening: Generally takes 3 to 4 days for bud to progress from first color to fully open flower.

*Bud just before opening*.—Quantity: Approximately 10. Shape: Ovoid. Length: Approximately 5.0 mm. Width: Approximately 3.0 mm. Texture: Densely pubescent. Color: 146C with a heavy overlay of 187A.

*Corolla*.—Shape: Rotate during the day, cupped at night. Diameter: Approximately 1.3 cm. Depth: Approximately 6.0 mm.

*Petals*.—Quantity: 5 to 6. Shape: Elliptic. Appearance: Matte. Margin: Minutely scalloped. Apex: Broadly acute. Base: Attenuate. Length: Approximately 7.0 mm. Width: Approximately 6.0 mm. Texture of upper and lower surfaces: Glabrous. Color of upper surface when first and fully open: 7A. Color of lower surface when first and fully open: 7D.

*Calyx*.—Shape: Pointed star. Diameter: Approximately 1.1 cm.

*Sepals*.—Quantity per flower: 5 to 6, fused at base. Shape: Lanceolate. Margin: Entire. Apex: Acute. Length: Approximately 6.0 mm. Width: Approximately 2.0 mm. Texture of upper (inner) surface: Densely glandular pubescent. Gland color: Colorless, transparent. Texture of lower (outer) surface: Densely pubescent. Color of upper and lower surfaces: 146C with a heavy overlay of 187A.

*Peduncle*.—Strength: Strong, flexible. Aspect: Acute angle to stem. Length: Approximately 1.0 cm. Diameter: Approximately 2.0 mm. Texture: Densely pubescent. Color: 146B with a heavy overlay of 187B.

*Reproductive organs*.—Androecium: Stamen quantity: 5 per flower. Stamen length: Approximately 4.0 mm, basal portion connate enclosing the ovary. Anther shape: Oblong, bilobed. Anther length: Approximately 1.0 mm. Anther color: 8B. Filament color: 7A. Pollen amount: Moderate. Pollen color: 7A. Gynoecium: Pistil quantity: 1 per flower. Pistil length: Approximately 4.0 mm. Stigma shape: Rounded. Stigma length: Less than 1.0 mm. Stigma color: 146D. Style length: Approximately 2.0 mm. Style color: Closest to 146D with a faint overlay of 187A. Ovary length: Approximately 1.5 mm. Ovary texture: Moderately pubescent at style attachment. Ovary color: Closest to but lighter than 146D.

Seed and fruit production: Neither seed nor fruit production has been observed.

Disease and pest resistance: Resistance to pathogens and pests common to *Lysimachia* has not been observed.

What is claimed is:

1. A new and distinct cultivar of *Lysimachia* plant named 'Firefly', substantially as herein illustrated and described.

* * * * *